United States Patent [19]

Kono

[11] Plant 4,071

[45] July 5, 1977

[54] CLEAR YELLOW MAY SHOESMITH

[76] Inventor: Yoshio Kono, 13200 Barbata Road, La Mirada, Calif. 90638

[21] Appl. No.: 617,525

[22] Filed: Sept. 29, 1975

[51] Int. Cl.[2] ..... A01H 5/00

[52] U.S. Cl. ..... Plt./78

[58] Field of Search ..... Plt./78

*Primary Examiner*—Robert E. Bagwill

*Attorney, Agent, or Firm*—James R. Cypher

[57] ABSTRACT

This invention relates to a sport of May Shoesmith chrysanthemum, which is distinguished therefrom by its clear yellow blossom color.

3 Drawing Figures

1

This invention relates to a new and distinct variety of chrysanthemum plant which is a sport of May Shoesmith, an unpatented commerical variety.

This sport was selected from a flowering of May Shoesmith in my commercial greenhouses in La Mirada, Calif., because of the yellow color compared to May Shoesmith. The color is a clear yellow with an absence of a gold undertone. Under fluorescent light the color is enhanced. The size of the flower is approximately ½-¾ inch smaller in diameter than May Shoesmith.

The plant has been revegetated and through repeated flowerings, the growth proved to be 2–3 inches shorter and a response bloom time of 2–3 days earlier than May Shoesmith. Flower petals exhibit several whiskers on the upper reverse tips of the petals, which are not objectionable to the eye. When grown under cooler night temperature the whiskers become more predominant.

This new sport is similar to May Shoesmith in the following characteristics:

1. Foliage shape
2. Heavy stem and growth

This new sport is different from May Shoesmith in the following characteristics:

1. Yellow color
2. ½–¾ inch smaller
3. 2–3 inches shorter in growth
4. 2–3 days earlier in response
5. Leaf appearance has more sheen Asexual reproduction of my new and distinct variety has proven to be consistent in:

1. Vegetative growth
2. Claims of flower characteristics
3. Leaf sheen

The overall growth characteristics may vary according to environmental conditions under which it is grown, however, here in La Mirada, Calif., it has been consistent as stated above.

It is recommended to flower from September to May for cut flower growers.

The accompanying photograph illustrates the color as being as true as possible with color illustrations of this type. The color of the new variety will be apparent in the photograph.

The color designation is by use of the Royal Horticulture Society color chart, R. F. Wilson, of the Royal Horticulture Society of London, England.

Plant:

*Botanical classification.*—*Chrysanthemum morifolium* Ramat.

*Origin.*—Selected from commercial flowering.

2

*Form.*—Herbaceous.

*Height.*—108 cm.

*Growth.*—Strong; vigorous; upright.

Leaf:

*Size.*—15 cm. × 7 cm.

*Shape.*—Lanceolate, deeply lobed.

*Texture.*—Smooth.

*Ribs & Veins.*—Prominent.

*Margin.*—Deeply lobed with serrations.

*Color.*—139A green group RHS.

Bud:

*Diameter.*—3 cm.

*Depth.*—1.5 cm.

*Color.*—7B yellow group RHS.

Flower color:

*Center of flower.*—7C yellow group RHS.

*Base of petal* (6.35 *mm from end*).—7C yellow group RHS.

*Inside of petal.*—7C yellow group RHS.

*Reverse of petal.*—7D yellow group RHS.

*Tonality from distance.*—7C yellow group RHS.

Other characteristics:

*Size of flower.*—14 cm. × 9 cm.

*Pollen.*—Visible.

*Disc florets.*—Present.

*Pistil.*—Present.

This new variety of chrysanthemum plant was compared with other sports of May Shoesmith (unpatented); namely, Bright Yellow Shoesmith, (U.S. Plant Pat. No. 3,486), Yellow May Shoesmith (U.S. Plant Pat. No. 3,280), and Sunshine (unpatented), after growing all of them under the same conditions in Fremont, Calif.

This new variety, Clear Yellow May Shoesmith, was compared with the other sports with readings being taken in September, October, and January. Clear Yellow May Shoesmith consistently flowers a few days earlier than the other sports when planted at the same time. There is a clear and distinct difference in color between Clear Yellow May Shoesmith and the other sports tested. A chart showing the color differences is set forth below:

| | CLEAR YELLOW MAY SHOESMITH | | | | |
|---|---|---|---|---|---|
| | 1 | 2 | 3 | 4 | 5 |
| CENTER OF FLOWER | 5C | 7D | 7C | 7B-C | 7B-C |
| BASE OF PETAL (¼" from end) | 3C | 5C | 5C | 5C | 5C |
| INSIDE OF PETAL | 3C | 5C | 5C | 5C | 5C |
| REVERSE OF PETAL | 2D | 2D | 5D | 5D | 8D |
| TONALITY FROM DISTANCE | 5C | 7D | 7C | 7C | 7C-D |

BRIGHT YELLOW MAY SHOESMITH NO. 1

| | 1 | 2 | 3 | 4 | 5 |
|---|---|---|---|---|---|
| CENTER OF FLOWER | 12B | 12A-B | 12A-B | 12A-B | 12B |
| BASE OF PETAL (¼" from end) | 5C | 7D | 7D | 7D | 7D |
| INSIDE OF PETAL | 5C | 7D | 7D | 7D | 7D |
| REVERSE OF PETAL | 5D | 5D | 6D | 8D | 8C |
| TONALITY FROM DISTANCE | 7D | 8B | 9C | 9C | 8A |

BRIGHT YELLOW MAY SHOESMITH NO. 2

| | 1 | 2 | 3 | 4 | 5 |
|---|---|---|---|---|---|
| CENTER OF FLOWER | 12B | 12A-B | 12A-B | 12A-B | 12B |
| BASE OF PETAL (¼" from end) | 6C | 7D-8B | 6C-7C | 6C-7C | 5C |
| INSIDE OF PETAL | 6C | 7C-8B | 6C-7C | 6C-7C | 5C |
| REVERSE OF PETAL | 5D | 6D | 6D | 5D | 8C |
| TONALITY FROM DISTANCE | 9C | 9C | 9B | 9B | 9B |

SUNSHINE

| | 1 | 2 | 3 | 4 | 5 |
|---|---|---|---|---|---|
| CENTER OF FLOWER | 7B | 7B | 9B | 9C | 8B |
| BASE OF PETAL (¼" from end) | 5C | 6C | 5C-6C | 6C | 6D-7D |
| INSIDE OF PETAL | 5C | 6C | 5C-6C | 6C | 6D-7D |
| REVERSE OF PETAL | 5D | 5D-6D | 5D | 5D | 8D |
| TONALITY FROM DISTANCE | 7D | 9C | 9B-9C | 8B | 8B |

YELLOW MAY SHOESMITH

| | 3 | 4 | 5 |
|---|---|---|---|
| CENTER OF FLOWER | 5D-6D | 5D-6D | 5D-6D |
| BASE OF PETAL (¼" from end) | 4C | 4C | 2D |
| INSIDE OF PETAL | 4C | 4C | 2D |
| REVERSE OF PETAL | 4D | 4D | 2D |
| TONALITY FROM DISTANCE | 5D-6D | 5D-6D | 5D-6D |

1.
(a) Date: 9-16-76
(b) Time: 10:25 A.M. – 1:30 P.M.
(c) Partly cloudy to sunny
(d) Sun to back
(e) Color chip held at 180° to flower
(f) Flower 90% open 2.
(a) Date: 9-19-76
(b) Time: 4:15 – 5:30 P.M.
(c) Balance of information same as No. 1

3.
(a) Date: 10-17-76
(b) Time: 12:30 – 2 P.M.
(c) Sunny
(d) Flower ⅓ open
(e) Balance of information same as No. 1

4.
(a) Date: 10-22-76
(b) Time: 1:00 – 2:30 P.M.
(c) Sunny
(d) Flower ⅔ – ¾ open
(e) Balance of information same as No. 1

5.
(a) Date: 10-22-76
(b) Time: 10 – 12:00 noon
(c) Inside fluorescent lighting (F96T12-CW Lifeline Sylvania)
(d) Flower ⅔ – ¾ open
(e) Balance of information same as No. 1

While it may be seen that there was a range of color differences of each and every variety opening upon the date the reading was taken, the time of day, the type of weather, the maturity of the flower and the degree of flower opening or whether the reading was taken indoors or outdoors, the same substantial degree of color difference between Clear Yellow May Shoesmith and the other sports remained constant.

It may be noted that the readings in the above chart do not match exactly with the color chart readings set forth in the patent specification of the patented sports. Further, the readings of this new variety grown in Fremont do not match exactly with this new variety of plants grown in La Mirada, Calif. This is to be expected since colors in chrysanthemums depend upon several conditions.

In addition to the clear color differences between this variety and the above sports, there are several differences as to form.

Yellow May Shoesmith (U.S. Plant Pat. No. 3,280) has a flower which is incurved, but not fully of incurving form. It has slight florets with broad ray florets. The florets are void of whiskers on the distal end. Bright Yellow May Shoesmith (U.S. Plant Pat. No. 3,486) and Sunshine (unpatented) both have an incurve but not fully incurving form. These also have slight skirted florets. Ray florets are more narrow than Yellow May Shoesmith (U.S. Plant Pat. No. 3,280). The florets are void of whiskers on the distal end.

This plant, Clear Yellow May Shoesmith, in distinct contrast to the other sports of May Shoesmith compared, has less formal incurving, more toward decorative form. It appears to have a higher ray floret count in the center than all of the other sports compared. The width of the ray floret is more narrow than the other sports described. Clear Yellow May Shoesmith also has a greater cupping of the floret through the length of the floret than the other sports described. Finally, the distal end of the floret of Clear Yellow May Shoesmith, in contrast to the other sports described, will have occasional whiskers.

The petals of Clear Yellow May Shoesmith were smaller in width and length than the petals of the other sports described. The petals compared from each variety were taken from medium petals approximately at a 45° angle from the center. The exact measurements are as follows:

| | Petal Width | Petal Length |
|---|---|---|
| YELLOW MAY SHOESMITH | 12.5 mm | 80 mm |
| BRIGHT YELLOW MAY SHOESMITH NO. 1 | 10 mm | 73.5 mm |
| BRIGHT YELLOW MAY SHOESMITH NO. 2 | 9 mm | 71 mm |
| SUNSHINE | 9 mm | 69 mm |
| CLEAR YELLOW MAY SHOESMITH | 7.5 mm | 65 mm |

This new variety of chrysanthemum plant when grown under the same growing conditions has a yellow flower 12.7 mm to 19.05 mm smaller than the parent May Shoesmith. The flowering tests with the known yellow May Shoesmith sports show that this new variety has a clearer yellow color which is more toward the yellow-green than toward the yellow-orange. The overall color exhibited an absence of a darker yellow. In regard to other characteristics, the distal end of the petal of the new variety will show occasional whiskers. Further, the new variety has a two to three day earlier response time than the parent and other known yellow May Shoesmith sports. Plant growth is 5.08 cm to 7.62 cm shorter. The leaf surface has a sheen compared to a flat surface on the yellow sports. The flower of the new variety is less formal incurving. The individual petals appear more narrow instead of U-shaped which is apparent in the other sports and also has a greater cupping through the length of the petal.

I claim:

1. A new and distinct variety of chrysanthemum plant, substantially as herein shown and descibed, characterized by a yellow flower 12.7 mm to 19.05 mm smaller than the parent May Shoesmith; having a clearer yellow color which is more toward the yellow-green than toward the yellow-orange; exhibiting an absence of a darker yellow; the distal end of the petal shows occasional whiskers; has a two to three day earlier response time than the parent and other known sports of the parent; plant growth is 5.08 cm to 7.62 cm shorter, the leaf surface has a sheen; the flower is less formal incurving; and the individual petals appear more narrow and exhibit greater cupping through the length of the petal.

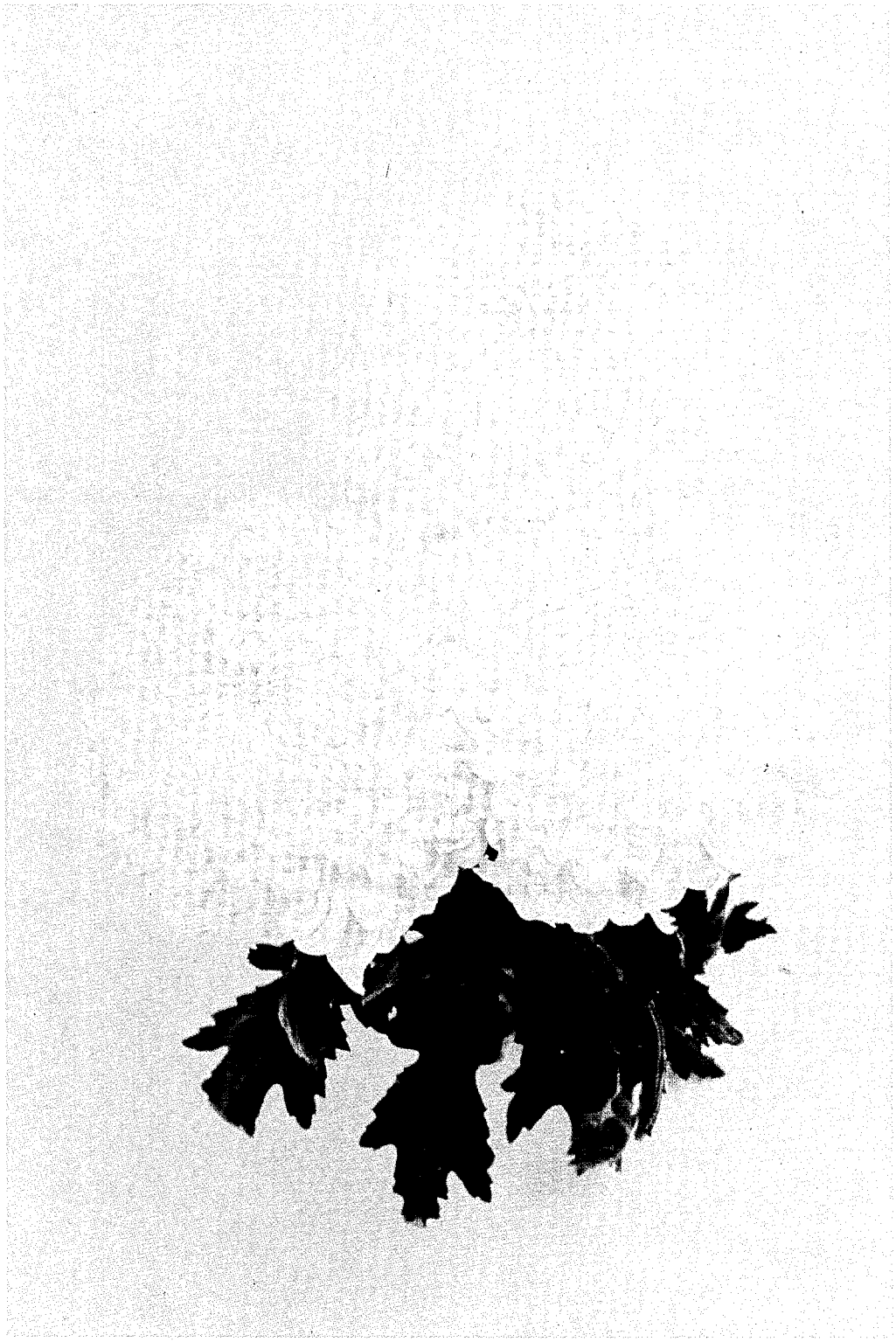

* * * * *